(12) United States Patent
François et al.

(10) Patent No.: US 6,555,544 B2
(45) Date of Patent: *Apr. 29, 2003

(54) AQUEOUS SUSPENSIONS OF SUBMICRON 9-HYDROXYRISPERIDONE FATTY ACID ESTERS

(75) Inventors: Marc Karel Jozef François, Kapellen (BE); Willy Maria Albert Carlo Dries, Merksplas (BE); Esther Dina Guido Basstanie, Zandhoven (BE)

(73) Assignee: Janssen Pharmaceutica, N.V. (BE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/530,687

(22) PCT Filed: Nov. 10, 1998

(86) PCT No.: PCT/EP98/07321

§ 371 (c)(1),
(2), (4) Date: May 2, 2000

(87) PCT Pub. No.: WO99/25354

PCT Pub. Date: May 27, 1999

(65) Prior Publication Data

US 2003/0064998 A1 Apr. 3, 2003

(30) Foreign Application Priority Data

Nov. 17, 1997 (EP) .............................. 97203568

(51) Int. Cl.$^7$ ................ A01N 43/90; A61K 31/519
(52) U.S. Cl. ............... 514/259.41; 514/259.1
(58) Field of Search .............. 424/422; 514/259.41, 514/259.1

(56) References Cited

U.S. PATENT DOCUMENTS 5,158,952 A * 10/1992 Janssen et al. .............. 514/258
6,077,843 A * 6/2000 Francois et al. ............ 514/528

FOREIGN PATENT DOCUMENTS

EP         368388         * 10/1989
WO     WO 97/44039        11/1997

* cited by examiner

Primary Examiner—Alton Pryor
(74) Attorney, Agent, or Firm—Mary Appollina

(57) ABSTRACT

The present invention is concerned with a pharmaceutical composition suitable as a depot formulation for administration via intramuscular or subcutaneous injection, comprising:

(1) as an active ingredient a therapeutically effective amount of a 9-hydroxy-risperidone fatty acid ester or a salt, or a stereoisomer or a stereoisomeric mixture thereof in submicron form and (2) a pharmaceutically acceptable carrier; wherein the pharmaceutically acceptable carrier is water and the active ingredient is suspended therein:

and with a process of preparing such a composition.

The invention further concerns such a pharmaceutical composition for use as a medicament in the treatment of psychosis, schizophrenia, schizoaffective disorders, non-schizophrenic psychoses, behavioural disturbances associated with neurodegenerative disorders, e.g. in dementia, behavioural disturbances in mental retardation and autism, Tourette's syndrome, bipolar mania, depression, anxiety.

7 Claims, No Drawings

AQUEOUS SUSPENSIONS OF SUBMICRON 9-HYDROXYRISPERIDONE FATTY ACID ESTERS

CROSS REFERENCE TO RELATED APPLICATIONS

This application is a National Stage application under 35 U.S.C. §371 of PCT/EP98/07321 filed Nov. 10, 1998, which claims priority from EP 97.203.568.7, filed Nov. 17, 1997.

The present invention is concerned with a pharmaceutical composition suitable as a depot formulation for administration via intramuscular or subcutaneous injection, comprising:

(1) as an active ingredient a therapeutically effective amount of a 9-hydroxy-risperidone fatty acid ester or a salt, or a stereoisomer or a stereoisomeric mixture thereof in submicron form and (2) a pharmaceutically acceptable carrier; wherein the pharmaceutically acceptable carrier is water and the active ingredient is suspended therein;

and with a process of preparing such a composition.

The invention further involves such a pharmaceutical composition for use as a medicament in the treatment of psychosis, schizophrenia, schizoaffective disorders, non-schizophrenic psychoses, behavioural disturbances associated with neurodegenerative disorders, e.g. in dementia, behavioural disturbances in mental retardation and autism, Tourette's syndrome, bipolar mania, depression, anxiety.

Risperidone is generic to 3-[2-[4-(6-fluoro-1,2-benzisoxazol-3-yl)-1-piperidinyl]ethyl]-6,7,8,9-tetrahydro-2-methyl-4H-pyrido[1,2-a]pyrimidin-4-one. The preparation and pharmacological activity thereof are described in EP-0,196,132 (corresponding to U.S. Pat. No. 4,804,663). Various conventional pharmaceutical dosage forms, including tablets, capsules, drops, suppositories, oral solutions and injectable solutions are exemplified therein. In practice, risperidone is normally administered as the base in a tablet or in a buffered, oral or intramuscular solution. Particular solutions for oral or intramuscular administration are described in WO-96/01652.

Risperidone is a highly potent drug having a relatively narrow therapeutic index. It may produce undesirable side effects on overdosage, most notably extra pyramidal syndrome (EPS) and to a lesser extent hypotension (due to peripheral alpha-adrenergic activity). For the purpose of producing an antipsychotic effect in a patient the total daily dose of risperidone ranges from about 2 to about 8 mg; for the alleviation of behavioral disturbances associated with neurodegenerative disorders the total daily dose is usually less and typically ranges from about 0.5 to about 2 mg. Inter-individual differences and co-medication may necessitate dose titrating in patients.

It is known that risperidone is metabolized to 9-hydroxyrisperidone which has a pharmacological profile and potency comparable with that of the parent drug risperidone, but which has a longer elimination half-life. Risperidone is distributed to and eliminated from the brain tissues more rapidly than its metabolite 9-hydroxy-risperidone. 9-hydroxyrisperidone, its enantiomeric forms and the $C_{2-20}$ alkanoic acid esters thereof are described in EP-0,368,388 (corresponding to U.S. Pat. Nos. 5,158,952 and 5,254,556). Said esters are considered to be potentially valuable prodrugs of the active metabolite of risperidone for use in depot formulations.

For a number of reasons, it is desirable to administer risperidone in a sustained or delayed release (depot) formulation which is effective over an extended period of time, preferably about 3 weeks or more, in particular about 1 month.

WO-94/25460 (corresponding to EP-0,697,019) relates to a first such depot formulation and concerns the risperidone pamoate salt, a poorly water-soluble salt form of risperidone, which may be suspended in a pharmaceutically acceptable carrier, such as water or an oil, and may be administered subcutaneously or intramuscularly. This salt, however, has pharmacokinetic properties which are suboptimal. The release of the active ingredient from the formulations appears to be too rapid, which results in relatively high initial plasma levels and an inadequate mean duration of action, both characteristics which should be improved upon in a truly effective depot formulation.

WO-95/13814 concerns sustained release formulations for parenteral administration wherein risperidone is microencapsulated in a biocompatible, biodegradable wall-forming material (e.g. a polymer such as dl-(polylactide-co-glycolide)). The micro-encapsulated formulations have suitable pharmacokinetic properties, but require sophisticated processes of preparation in a purpose-built plant.

PCT/EP97/02504 discloses aqueous suspensions of 9-hydroxyrisperidone fatty acid esters in water wherein the prodrug of the active ingredient is in micronized fonn. Unexpectedly, these formulations prove to be far too longlasting in humans to be therapeutically useful.

Consequently, there is still a need for an effective and readily available depot formulation of risperidone or a risperidone-like compound.

Nanoparticles are well known in the prior art, having been described, for example, in EP-A-0,499,299. These particles consist essentially of a crystalline drug substance having a surface modifier absorbed on the surface of the particles such that the effective average particle size is less than about 400 nm. It is also known that said particles are particularly useful to formulate poorly water soluble active ingredients.

The present invention results from the investigations into the development of an efficient, well-tolerated, sustained or delayed release (depot) formulation of a 9-hydroxyrisperidone alkanoic acid ester which is therapeutically effective for at least three weeks or more, in particular about 1 month. By the expression "effective for at least three weeks or more", one means that the plasma level of the active ingredient, 9-hydroxyrisperidone (free alcohol liberated by hydrolysis from the alkanoic acid ester), should be above approximately 10 ng/ml. On the other hand, said plasma level should remain at all times below a threshold value of approximately 100 ng/ml in order for one to call the formulation "efficient". The threshold value is the mean plasma level during a considerable period of time, e.g. for more than 15 minutes, above which patients may experience undesirable side effects, or conversely, the value of the plasma level under which the systemic tolerance of the formulation in question is still acceptable. The threshold value does not hold for transient, high plasm levels during a short period of time, e.g. for less than 15 minutes, which are due, for example to unexpected burst-release of the active ingredient.

Both of the foregoing features—plasma levels above a minimal therapeutical concentration but below a side-effect producing threshold value—are considered to be basic requirements that a contemporary depot formulation should fulfil in order to be acceptable for the intended patients. Limiting the number of drug administrations and the occurrence of undesirable side effects after each administration will undoubtedly improve the patients' compliance with the therapy. However, beyond these basic requirements, a number of further desiderata can be identified which would further improve patients' compliance; the two most notable being good local tolerance and ease of administration.

Good local tolerance means minimal irritation and inflammation at the site of injection; ease of administration refers to the size of needle and length of time required to administer a dose of a particular drug formulation. In addition, depot formulations should be stable and have a shelf-life of at least two years under normal conditions.

The investigations into the development of an efficient, well-tolerated, sustained or delayed release (depot) formulation of a 9-hydroxyrisperidone alkanoic acid ester which fulfils the above mentioned requirements, led to the finding that a pharmaceutical composition suitable as a depot formulation for administration by intramuscular or subcutaneous injection should comprise:

a dispersion of particles consisting essentially of a therapeutically effective amount of a crystalline 9-hydroxyrisperidone fatty acid ester having the formula

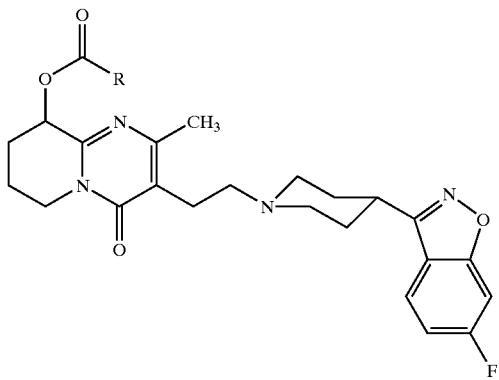

or a salt, or a stereoisomer or a stereoisomeric mixture thereof, wherein R represents a straight $C_{9-19}$ alkyl radical; having a surfactant absorbed to the surface thereof in an amount effective in maintaining a specific surface area >4 $m^2/g$ (corresponding to an effective average particle size of less than 2,000 nm), in a pharmaceutically acceptable carrier comprising water.

Surprisingly, it appears that aqueous suspensions of micronized 9-hydroxyrisperidone $C_{10-20}$ alkanoic acid esters (wherein R represents a straight $C_{9-19}$ alkyl radical) have an exceptionally longlasting effect in humans, but not in test animals, in particular dogs. This is quite unexpected since the pharmacokinetics of drugs in humans and in dogs are often comparable. The pharmacokinetic properties in humans of the aqueous suspensions of 9-hydroxyrisperidone alkanoic acid esters depend on the particle size to a much larger extent than previously held possible.

$C_{10-20}$ alkanoic acids are selected from the group consisting of decanoic (capric), undecanoic, dodecanoic (lauric), tridecanoic, tetradecanoic (myristic), pentadecanoic, hexadecanoic (palmitic), heptadecanoic, octadecanoic (stearic), nonadecanoic and eicosanoic acid. The ester having a $C_{15}$ (pentadecyl) chain and the active ingredient corresponding thereto being the 9-hydroxyrisperidone palmitate ester was found to be the superior ester from a pharmacokinetic, as well as from a tolerance point of view.

The nanoparticles of the present invention have a surfactant or surface modifier adsorbed on the surface thereof in an amount sufficient to maintain a specific surface area >4 $m^2/g$ (i.e. corresponding to an average particle size of less than 2,000 nm), preferably the specific surface area >6 $m^2/g$, and in particular is in the range from 10 to 16 $m^2/g$. Useful surface modifiers are believed to include those which physically adhere to the surface of the active agent but do not chemically bond thereto.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants. Representative examples of excipients include gelatin, casein, lecithin (phosphatides), gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available Tweens™, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethylcellulose phthalate, noncrystalline cellulose, magnesium aluminate silicate, triethanolamine, polyvinyl alcohol (PVA), poloxamers, tyloxapol and polyvinylpyrrolidone (PVP). Most of these excipients are described in detail in the *Handbook of Pharmaceutical Excipients*, published jointly by the American Pharmaceutical Association and The Pharmaceutical Society of Great Britain, the Pharmaceutical Press, 1986. The surface modifiers are commercially available and/or can be prepared by techniques known in the art. Two or more surface modifiers can be used in combination.

Particularly preferred surface modifiers include polyvinylpyrrolidone; tyloxapol; poloxamers, such as Pluronic™ F68, F108 and F127 which are block copolymers of ethylene oxide and propylene oxide available from BASF; poloxamines, such as Tetronic™ 908 (T908) which is a tetrafunctional block copolymer derived from sequential addition of ethylene oxide and propylene oxide to ethylenediamine available from BASF; dextran; lecithin; Aerosol OT™ (AOT) which is a dioctyl ester of sodium sulfosuccinic acid available from Cytec Industries; Duponol™ P which is a sodium lauryl sulfate available from DuPont; Triton™ X-200 which is an alkyl aryl polyether sulfonate available from Rohm and Haas; Tweens™ 20, 40, 60 and 80 which are polyoxyethylene sorbitan fatty acid esters available from ICI Speciality Chemicals; Span™ 20, 40, 60 and 80 which are sorbitan esters of fatty acids; Arlacel™ 20, 40, 60 and 80 which are sorbitan esters of fatty acids available from Hercules, Inc.; Carbowax™ 3550 and 934 which are polyethylene glycols available from Union Carbide; Crodesta™ F110 which is a mixture of sucrose stearate and sucrose distearate available from Croda Inc.; Crodesta™ SL-40 which is available from Croda, Inc.; hexyldecyl trimethyl ammonium chloride (CTAC); bovine serum albumin and SA90HCO which is $C_{18}H_{17}CH_2(CON(CH_3)CH_2(CHOH)_4CH_2OH)_2$. The surface modifiers which have been found to be particularly useful include tyloxapol and a poloxamer, preferably, Pluronic™ F108 and Pluronic™ F68.

Pluronic™ F108 corresponds to poloxamer 338 and is the polyoxyethylene, polyoxypropylene block copolymer that conforms generally to the formula $HO[CH_2CH_2O]_x[CH(CH_3)CH_2O]_y[CH_2CH_2O]_zH$ in which the average values of x, y and z are respectively 128, 54 and 128. Other commercial names of poloxamer 338 are Hodag Nonionic™ 1108-F available from Hodag, and Synperonic™ PE/F108 available from ICI Americas.

The optimal relative amount of the antipsychotic agent and the surface modifier depends on various parameters. The optimal amount of the surface modifier can depend, for example, upon the particular antipsychotic agent and surface modifier selected, the critical micelle concentration of the surface modifier if it forms micelles, the surface area of the antipsychotic agent, etc. The specific surface modifier preferably is present in an amount of 0.1 to 1 mg per square meter surface area of the antipsychotic agent. In case 9-hydroxyrisperidone palmitate is used as antipsychotic agent and Pluronic™ F108 as a surface modifier, a relative amount (w/w) of both ingredients of approximately 6:1 is preferred.

As used herein, an effective average particle size of less than 2,000 nm means that at least 90% of the particles have a diameter of less than 2,000 nm when measured by art-known conventional techniques, such as sedimentation field flow fractionation, photon correlation spectroscopy or disk centrifugation. With reference to the effective average particle size, it is preferred that at least 95% and, more preferably, at least 99% of the particles have a particle size of less than the effective average particle size, e.g. 2,000 nm. Most preferably, essentially all of the particles have a size of less than 2,000 nm.

The particles of this invention can be prepared by a method comprising the steps of dispersing an antipsychotic agent in a liquid dispersion medium and applying mechanical means in the presence of grinding media to reduce the particle size of the antipsychotic agent to an effective average particle size of less than 2,000 nm. The particles can be reduced in size in the presence of a surface modifier. Alternatively, the particles can be contacted with a surface modifier after attrition.

A general procedure for preparing the particles of this invention includes (a) obtaining an antipsychotic agent in micronized form;
(b) adding the micronized antipsychotic agent to a liquid medium to form a premix; and
(c) subjecting the premix to mechanical means in the presence of a grinding medium to reduce the effective average particle size.

The selected antipsychotic agent in micronized form is obtained commercially or prepared using techniques known in the art. It is preferred that the particle size of the micronized antipsychotic agent be less than about 100 μm as determined by sieve analysis. If the particle size of the micronized antipsychotic agent is greater than about 100 μm, then it is preferred that the particles of the antipsychotic agent be reduced in size to less than 100 μm.

The micronized antipsychotic agent can then be added to a liquid medium in which it is essentially insoluble to form a premix. The concentration of the antipsychotic agent in the liquid medium (weight by weight percentage) can vary widely and depends on the selected antipsychotic agent, the selected surface modifer and other factors. Suitable concentrations of antipsychotic agent in compositions vary between 0.1 to 60%, preferably is from 0.5 to 30%, and more preferably, is approximately 7% (w/v).

A more preferred procedure involves the addition of a surface modifier to the premix prior to its subjection to mechanical means to reduce the effective average particle size. The concentration of the surface modifier (weight by weight percentage) can vary from 0.1% to 90%, preferably from 0.5% to 80%, and more preferably is approximately 7% (w/v).

The premix can be used directly by subjecting it to mechanical means to reduce the effective average particle size in the dispersion to less than 2,000 nm. It is preferred that the premix be used directly when a ball mill is used for attrition. Alternatively, the antipsychotic agent and, optionally, the surface modifier, can be dispersed in the liquid medium using suitable agitation such as, for example, a roller mill or a Cowles type mixer, until a homogeneous dispersion is achieved.

The mechanical means applied to reduce the effective average particle size of the antipsychotic conveniently can take the form of a dispersion mill. Suitable dispersion mills include a ball mill, an attritor mill, a vibratory mill, a planetary mill, media mills—such as a sand mill and a bead mill. A media mill is preferred due to the relatively shorter milling time required to provide the desired reduction in particle size. For media milling, the apparant viscosity of the premix preferably is anywhere between 0.1 and 1 Pa·s. For ball milling, the apparant viscosity of the premix preferably is anywhere etween 1 and 100 mPa·s.

The grinding media for the particle size reduction step can be selected from rigid media preferably spherical or particulate in form having an average size less than 3 mm and, more preferably, less than 1 mm. Such media desirably can provide the particles of the invention with shorter processing times and impart less wear to the milling equipment. The selection of the material for the grinding media is believed not to be critical. However, 95% ZrO stabilized with magnesia, zirconium silicate, and glass grinding media provide particles having levels of contamination which are believed to be acceptable for the preparation of pharmaceutical compositions. Further, other media, such as polymeric beads, stainless steel, titania, alumina and 95% ZrO stabilized with yttrium, are useful. Preferred grinding media have a density greater than 2.5 g/cm$^3$ and include 95% ZrO stabilized with magnesia and polymeric beads.

The attrition time can vary widely and depends primarily upon the particular mechanical means and processing conditions selected. For rolling mills, processing times of up to two days or longer may be required.

The particles must be reduced in size at a temperature which does not significantly degrade the antipsychotic agent. Processing temperatures of less than 30 to 40° C. are ordinarily preferred. If desired, the processing equipment may be cooled with conventional cooling equipment. The method is conveniently carried out under conditions of ambient temperature and at processing pressures which are safe and effective for the milling process.

The surface modifier, if it was not present in the premix, must be added to the dispersion after attrition in an amount as described for the premix above. Thereafter, the dispersion can be mixed by, for example, shaking vigorously. Optionally, the dispersion can be subjected to a sonication step using, for example, a ultrasonic power supply.

Aqueous compositions according to the present invention conveniently further comprise a suspending agent and a buffer, and optionally one or more of a preservative and an isotonizing agent. Particular ingredients may function as two or more of these agents simultaneously, e.g. behave like a preservative and a buffer, or behave like a buffer and an isotonizing agent.

Suitable suspending agents for use in the aqueous suspensions according to the present invention are cellulose derivatives, e.g. methyl cellulose, sodium carboxymethyl cellulose and hydroxypropyl methyl cellulose, polyvinylpyrrolidone, alginates, chitosan, dextrans, gelatin, polyethylene glycols, polyoxyethylene- and polyoxypropylene ethers. Preferably sodium carboxymethyl cellulose is used in a concentration of 0.5 to 2%, most preferably 1% (w/v). Suitable wetting agents for use in the aqueous suspensions according to the present invention are polyoxyethylene derivatives of sorbitan esters, e.g. polysorbate 20 and polysorbate 80, lecithin, polyoxyethylene- and polyoxypropylene ethers, sodium deoxycholate. Preferably polysorbate 20 is used in a concentration of 0.5 to 3%, more preferably 0.5 to 2%, most preferably 1.1% (w/v).

Suitable buffering agents are salt of weak acids and should be used in amount sufficient to render the dispersion neutral to very slightly basic (up to pH 8.5), preferably in the pH range of 7 to 7.5. Particularly preferred is the use of a mixture of disodium hydrogen phosphate (anhydrous) (typically about 0.9% (w/v)) and sodium dihydrogen phosphate monohydrate (typically about 0.6% (w/v)). This buffer also renders the dispersion isotonic and, in addition, less prone to flocculation of the ester suspended therein.

Preservatives are antimicrobials and anti-oxidants which can be selected from the group consisting of benzoic acid, benzyl alcohol, butylated hydroxyanisole, butylated hydroxytoluene, chlorbutol, a gallate, a hydroxybenzoate, EDTA, phenol, chlorocresol, metacresol, benzethonium chloride, myristyl-γ-piccolinium chloride, phenylmercuric acetate and thimerosal. In particular, it is benzyl alcohol which can be used in a concentration up to 2% (w/v), preferably up to 1.5% (w/v).

Isotonizing agents are, for example, sodium chloride, dextrose, mannitol, sorbitol, lactose, sodium sulfate. The suspensions conveniently comprise from 0 to 10% (w/v) isotonizing agent. Mannitol may be used in a concentration from 0 to 7% More preferably, however, from about 1 to about 3% (w/v), especially from about 1.5 to about 2% (w/v) of one or more electrolytes are used to render the suspension isotonic, apparently because ions help to prevent flocculation of the suspended ester. In particular electrolytes of the buffer serve as isotonizing agent.

A particularly desirable feature for an injectable depot formulation relates to the ease with which it can be administered. In particular such an injection should be feasible using a needle as fine as possible in a span of time which is as short as possible. This can be accomplished with the aqueous suspensions of the present invention by keeping the viscosity below about 75 mPa·s, preferably below 60 mPa·s. Aqueous suspensions of such viscosity or lower can both easily be taken up in a syringe (e.g. from a vial), and injected through a fine needle (e.g a 21 G 1½, 22 G 2 or 22 G 1¼ needle).

Ideally, aqueous suspensions according to the present invention will comprise as much prodrug as can be tolerated so as to keep the injected volume to a minimum, and as little of the other ingredients as possible. In particular, such a composition will comprise by weight based on the total volume of the composition:

(a) from 3 to 20% (w/v) of the prodrug;

(b) from 0.5 to 2% (w/v) of a wetting agent;

(c) one or more buffering agents sufficient to render the composition neutral to very slightly basic (pH 8.5);

(d) from 0.5 to 2% (w/v) of a suspending agent;

(e) up to 2% (w/v) preservatives; and (f) water q.s. ad 100%.

In view of the usefulness of 9-hydroxyrisperidone in the treatment of a number of disorders, the present invention also concerns a pharmaceutical composition as described hereinbefore for use as a medicament in the treatment of psychosis, schizophrenia, schizoaffective disorders, non-schizophrenic psychoses, behavioural disturbances associated with neurodegenerative disorders, e.g. in dementia, behavioural disturbances in mental retardation and autism, Tourette's syndrome, bipolar mania, depression, anxiety.

In addition, the present invention concerns the use of a composition as described hereinbefore for the preparation of a medicament for treating psychosis, schizophrenia, schizoaffective disorders, non-schizophrenic psychoses, behavioural disturbances associated with neurodegenerative disorders, e.g. in dementia, behavioural disturbances in mental retardation and autism, Tourette's syndrome, bipolar mania, depression, anxiety.

The present invention further concerns a method of treating warm-blooded animals, in particular humans suffering from psychosis, schizophrenia, schizoaffective disorders, non-schizophrenic psychoses, behavioural disturbances associated with neurodegenerative disorders, e.g. in dementia, behavioural disturbances in mental retardation and autism, Tourette's syndrome, bipolar mania, depression, anxiety, said method comprising the administration of a therapeutically effective amount of an, aqueous suspension as described hereinbefore. Typically, said formulation will be administered approximately every three weeks or even at longer intervals where possible. The dosage should range from about 2 to 4 mg/kg body weight.

The following examples are intended to illustrate the present invention.

EXPERIMENTAL PART

A. Preparation of 9-hydroxyrisperidone palmitate ester

N,N'-Dicyclohexylcarbodiimide (1.39 g; 6.8 mmol) was added to a solution of hexadecanoic acid (1.54 g; 6 mmol) in dichloromethane (140 ml) and stirred at room temperature for 10 minutes. 9-hydroxyrisperidone (2.13 g; 5 mmol) was added to the reaction mixture, followed by 4-pyrrolidinopyridine (93 mg; 0.63 mmol). The mixture was stirred for three days at room temperature. Water (200 ml) was added to the reaction mixture and this was extracted three times with chloroform (100 ml). The combined organic layers were dried (MgSO$_4$), filtered, and evaporated. The mixture was triturated in diisopropylether (100 ml), filtered and recrystalized in isopropanol (60 ml). The crystals were filtered off and dried, yielding 9-hydroxyrisperidone palmitate ester (2.67 g; 80.4%).

B. Composition Examples

The formulations hereunder were prepared according to the following general recipe: The surfactant, suspending agent and buffer were dissolved by stirring in water at room temperature and the solution was sterilized by heating during 30 minutes at 121° C. The active ingredient (micronized) was sterilized by gamma irradiation at 25 kGY and suspended in the previously prepared solution under sterile conditions. Appropriate glass vials were filled to about 30% of their total volume with the suspension and with the grinding medium, and then rolled at about 50 rpm for several hours. The submicron formulations were then sieved to remove the grinding medium and stored under sterile conditions. Formulation A (micronized) was rolled for 0 hours, B for 4 hours, C for 7 hours and D for 38 hours.

| Formulation (w/v) | |
|---|---|
| 9-hydroxyrisperidone palmitate | 7.02% (4.5% 9-hydroxyrisperidone) |
| polysorbate 20 | 1.1% |
| sodium carboxymethyl cellulose 30 mPa.s | 1% |
| benzyl alcohol parenteral | 1.5% |
| disodium hydrogen phosphate anhydrous | 0.9% |

-continued

| Formulation (w/v) | |
|---|---|
| sodium dihydrogen phosphate monohydrate | 0.6% |
| water q.s. ad | 100% |

Viscosity and pH values for each of the thus obtained submicron dispersion A–D were as follows:

| Formulation | pH | viscosity |
|---|---|---|
| A | 8.19 | ±7 mPa.s |
| B | 7.9 | ±8 mPa.s |
| C | 8.02 | ±9 mPa.s |
| D | 7.98 | ±10 mPa.s |

Particle size distribution was measured using a Mastersizer X and specific surface area using a Mastersizer S. The following values were obtained for formulations A–D

| | Particle size ($\mu$m) | | | |
|---|---|---|---|---|
| Formulation | 10% | 50% | 90% | specific surface area (m$^2$/g) |
| A | 2.51 | 6.03 | 7.64 | 1.3 |
| B | 0.62 | 1.38 | 6.83 | 6.5 |
| C | 0.52 | 0.74 | 1.15 | 13.5 |
| D | 0.43 | 0.52 | 0.65 | >15 |

Formulations C and D were put on a three month stability test and the following values were obtained for the stored formulations C and D:

| | Particle size ($\mu$m) | | | |
|---|---|---|---|---|
| Formulation | 10% | 50% | 90% | specific surface area (m$^2$/g) |
| C | 0.27 | 0.40 | 0.62 | 13.5 |
| D | 0.52 | 0.75 | 1.18 | not determined |

C. Pharmacological Examples

C.1. Pharmacological Testing of F1 and Analogous Oil Formulations.

Each of the four formulations A–D were administered to four beagle dogs intramuscularly in the m. bicepsfemuris of the left hind paw at 2.5 mg/kg bodyweight using a 21 G 1½ BD Microlance needle; syringability posed no problem. Blood samples were withdrawn during 2 months in order to determine 9-hydroxy risperidone plasma levels. The following pharmacokinetic parameters were calculated from the experimental data (mean±S.D.):

| formulation | $C_{max}$ (ng/ml) | $T_{max}$ (days) | $AUC_{0-t}$ (ng · h/ml) |
|---|---|---|---|
| A | 41.1 (±22.1) | 12 (±5) | 19487 (±7697) |
| B | 86.4 (±30.5) | 7 (±3) | 25769 (±9782) |
| C | 139 (±33) | 1.8 (±1.5) | 28603 (±4305) |
| D | 132 (±60) | 6.3 (±1.5) | 34852(±14055) |

What is claimed is:

1. A pharmaceutical composition suitable as a depot formulation for administration by intramuscular or subcutaneous injection, comprising a dispersion of particles consisting essentially of a therapeutically effective amount of a crystalline 9-hydroxyrisperidone fatty acid ester having the formula or a salt, or a stereoisomer or a stereoisomeric mixture thereof, wherein R represents a straight $C_{15}$ (pentadecyl) chain and the active ingredient is 9-hydroxyrisperidone palmitate ester; having a surfactant adsorbed to the surface thereof in an amount effective in maintaining a specific surface area >4 m$^2$/g (corresponding to an effective average particle size of less than 2,000 nm) in a pharmaceutically acceptable carrier comprising water.

2. A composition according to claim 1 wherein the composition further comprises a suspending agent, and optionally one or more of a preservative, a buffer and an isotonizing agent.

3. A composition according to claim 2 wherein the suspending agent is sodium carboxymethyl cellulose and the surfactant is polysorbate 20.

4. A composition according to ciaim 3 wherein the preservative is benzyl alcohol and the isotonizing agent is mannitol or a phosphate buffer.

5. A composition according to claim 1 having a viscosity of less than 75 mPa·s.

6. A composition according to claim 1 comprising by weight based on the total volume of the composition:
   (a) from 3 to 20% (w/v) of the 9-hydroxyrisperidone fatty acid ester having the formula or a salt, or a stereoisomer or a stereoisomer mixture thereof;
   (b) from 0.5 to 2% (+/v) of a wetting agent;
   (c) one or more buffering agents sufficient to render the composition neutral to very slightly basic (up to pH 8.5);
   (d) from 0.5 to 2% (w/v) of a suspending agent;
   (e) up to 2% (w/v) preservatives; and
   (f) water q.s. ad 100%.

7. A method for treating psychosis, schizophrenia, schizoaffective disorders, non-schizophrenic psychoses, behavioural disturbances associated with dementia, behavioural disturbances in mental retardation and autism, Tourette's syndrome, bipolar mania, depression, or anxiety in a warm-blooded animal in need thereof comprising administering to the animal a therapuetically effective amount of the composition of claim 1.

* * * * *

UNITED STATES PATENT AND TRADEMARK OFFICE
CERTIFICATE OF CORRECTION

PATENT NO. : 6,555,544 B2
DATED : April 29, 2003
INVENTOR(S) : Francois et al.

It is certified that error appears in the above-identified patent and that said Letters Patent is hereby corrected as shown below:

Column 10,
Line 38, "ciaim" should read -- claim --.
Line 50, "(+/v)" should read -- (w/v) --.

Signed and Sealed this

Twenty-third Day of September, 2003

JAMES E. ROGAN
*Director of the United States Patent and Trademark Office*